(12) United States Patent
Bonnin et al.

(10) Patent No.: US 8,876,834 B2
(45) Date of Patent: Nov. 4, 2014

(54) DEVICE FOR THE INJECTION OF BONE CEMENT, COMPRISING AN OVERPRESSURE LOCKING SYSTEM

(75) Inventors: Freddy Bonnin, Toulouse (FR); Alain Leonard, Caixon (FR)

(73) Assignee: Teknimed, Vic-en-Bigorre Cedex (FR)

( * ) Notice: Subject to any disclaimer, the term of this patent is extended or adjusted under 35 U.S.C. 154(b) by 174 days.

(21) Appl. No.: 13/697,820

(22) PCT Filed: Nov. 16, 2011

(86) PCT No.: PCT/FR2011/052666
§ 371 (c)(1),
(2), (4) Date: Nov. 14, 2012

(87) PCT Pub. No.: WO2012/066238
PCT Pub. Date: May 24, 2012

(65) Prior Publication Data
US 2013/0079786 A1    Mar. 28, 2013

(30) Foreign Application Priority Data
Nov. 16, 2010   (FR) ..................................... 10 59426

(51) Int. Cl.
*A61B 17/58* (2006.01)
*A61B 17/60* (2006.01)
*A61F 2/00* (2006.01)
*A61B 17/88* (2006.01)

(52) U.S. Cl.
CPC ......... *A61B 17/8822* (2013.01); *A61B 17/8819* (2013.01); *A61B 17/8827* (2013.01)
USPC ............................................................ 606/94

(58) Field of Classification Search
USPC ...................................................... 606/92–94
See application file for complete search history.

(56) References Cited

U.S. PATENT DOCUMENTS

| 4,498,904 A | 2/1985 | Turner et al. |
| 2002/0013553 A1 * | 1/2002 | Pajunk et al. ................ 604/187 |
| 2003/0018339 A1 | 1/2003 | Higueras et al. |
| 2004/0204715 A1 | 10/2004 | Evans et al. |

FOREIGN PATENT DOCUMENTS

EP    1 400 213 A1    3/2004

* cited by examiner

*Primary Examiner* — Sameh Boles
(74) *Attorney, Agent, or Firm* — Birch, Stewart, Kolasch & Birch, LLP

(57) ABSTRACT

The invention relates to a device for the injection of a bone cement. The invention comprises a container provided with one end including an outlet and a second end that receives a piston. The piston is moved by means of an injection screw that projects from the container body and engages with gripping means comprising injection screw rotation means that can self-lock depending on the pressure exerted inside the container body, said rotation means comprising a handle which is provided with a passage that receives the injection screw and which is hinged thereto by means of a pair of male/female disks. One disk is known as the drive disk and moves integrally with the rotation movements of the handle, while the other disk is known as the driven disk, said drive disk coming into contact with the driven disk in response to a compressive force exerted on the distal part of the injection screw.

9 Claims, 6 Drawing Sheets

Figure 1:
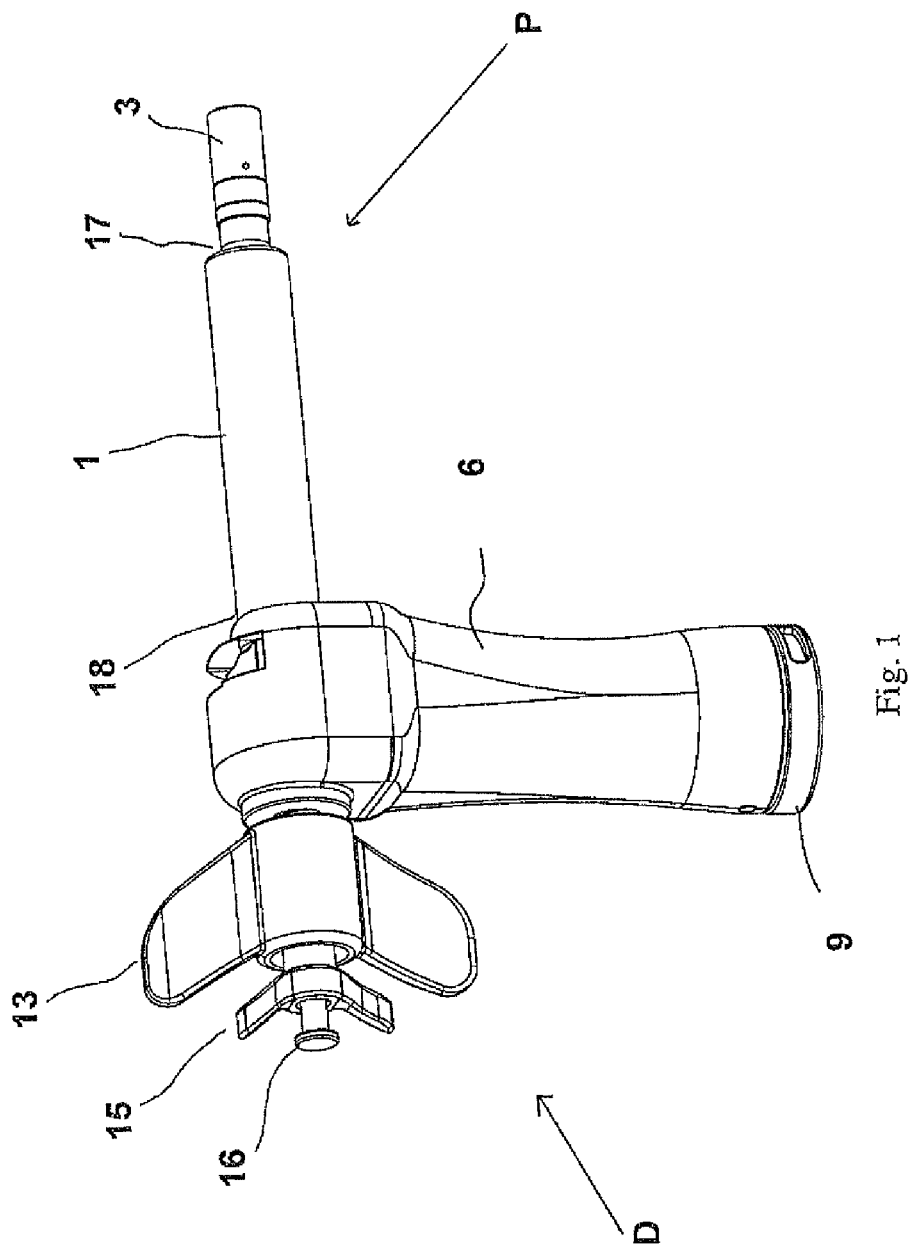

DEVICE FOR THE INJECTION OF BONE CEMENT, COMPRISING AN OVERPRESSURE LOCKING SYSTEM

The present invention relates to a medical device for injecting bone cement.

The injection of bone cement is carried out in various operations to strengthen the structure of the bone after trauma, natural wear or even in the case of degenerative disease. The cements used in these operations are of variable composition, generally based on methacrylate polymers combined with other additives depending on the applications envisaged. The viscosity of these compositions is also variable.

PRIOR ART

Various devices have been proposed to facilitate the injection of bone cement during these operations. The injection must be capable of being carried out with precision and safety. One of the difficulties is to obtain an even flow of bone cement through the injection syringe.

US Patent application 2002/013553 describes a device using a syringe mounted on a handle wherein the piston can be set in motion by means of a screw bearing on the handle and converting the rotational movements performed by the operator into a longitudinal displacement resulting in a progression of the piston inside the syringe.

This device has the advantage of enabling the operator to perform an injection in a progressive and regular manner, the cement being precisely ejected as the pressure increases within the syringe under the effect of the rotational movements applied by the operator.

However, a major drawback is related to the use of this device in the case where the operator applies too large a number of rotations to the screw. This generates an overpressure inside the syringe causing an excess flow of cement in the best case, or even causing the walls of the syringe to rupture if the overpressure is truly excessive.

The consequences of this may be critical for the continued performance of the operation and thus for the health of the patient.

Other devices have been described in patent applications US 2004/0204715, US 2003/018339, EP 1400213 and U.S. Pat. No. 4,498,904, but the systems disclosed in these applications do not include mechanisms to achieve precise injection of bone cement while at the same avoiding the occurrence of overpressure in the container. In particular, none of these documents describes the interaction of a male disk coming into contact with a female disk under the effect of a compressive force exerted on the distal part of the injection screw so as to self-lock depending on the pressure within the container.

BRIEF DESCRIPTION

The present invention aims to overcome the drawbacks of the prior art by proposing a new device for the injection of bone cement enabling the cement to be discharged progressively and evenly through a syringe associated with an injection screw, without risk of generating overpressure inside the syringe. The device according to the present invention thus makes it possible to avoid reaching a threshold pressure level which can be determined by the operator by means of a drive system capable of self-locking, that is to prevent the progression of the piston in the syringe, in case of overpressure inside the container. The object of the device according to the present invention is to obtain a perfectly controlled injection in terms of flowrate without risk of rupture or cracking of the injection equipment.

DETAILED DESCRIPTION OF THE INVENTION

More precisely, the device according to the invention comprises a container for receiving the said bone cement, having a first end comprising an outlet aperture for the injection of cement and a second end receiving a piston capable of performing longitudinal translational movements inside the body of the container, the said piston being set in motion via an injection screw projecting from the body of the container and engaging with gripping means designed to be placed integrally in contact with the container, characterised in that it comprises means for rotatably driving the injection screw capable of self-locking depending on the pressure inside the container body, the said means for rotatably driving the injection screw comprising a handle having a passage receiving the injection screw and articulated therewith via a pair of male/female disks, one of the two disks, referred to as the driving disk, being integral with the rotational movements of the handle and designed to perform translational movements on the longitudinal axis of the passage in the handle, the other disk, referred to as the driven disk, being integral with the rotational movements of the injection screw, the driving disk coming into contact with the driven disk under the effect of a compressive force exerted on the distal part of the injection screw.

In a particular embodiment of the invention, the two disks come into contact with one another by means of a compression spring having one end in abutment at the distal part of the injection screw, the other end of the spring coming into contact, directly or indirectly, with the driving disk. For example, the other end of the spring can come into contact with the injection handle such that the latter transmits the compressive force received by the spring to the driving disk. The driving disk is therefore placed in contact with the driven disk with a greater or lesser force depending on the degree to which the compression spring is stretched. Depending on the degree of pressure exerted inside the container, the force transmitted by the compression spring is or is not sufficient to enable the driving disk to cause the driven disk to move.

Advantageously, the distal part of the injection screw has clamping means enabling the compression distance of the spring to be adjusted. Depending on the selected distance it is thus possible to obtain a greater or lesser sensitivity of the device, that is to say locking of the driving means which may take place at relatively low levels of pressure inside the container.

Specifically, the greater the compression distance, within the limit of a compression of the spring at the minimum, the lower the force exerted by the spring on the driving disk (or on the injection handle). For this reason, the engagement of the driving disk on the driven disk only causes the injection screw to rotate when a relatively low level of pressure is present inside the container. Beyond this threshold pressure, the force exerted by the compression spring on the driving disk is not sufficient to move the driven disk and therefore the injection screw itself.

Conversely, if the compression distance is reduced to the minimum, that is so that the compression spring is able to stretch at the minimum, the rotational movements are transmitted more directly to the driving disk (or the injection handle). The latter causes the driven disk to move with a minimum damping effect. The driven disk thus causes the injection screw to move until much higher pressure levels appear within the container.

It is thus possible to precisely select the most appropriate compression distance of the spring by a simple adjustment of the clamping means, according to the type of operation to be performed, so as to obtain an injection of cement as even and precise as possible depending on the viscosity of the bone cement and the mechanical properties of the compression spring.

In a particular embodiment, the gripping means of the device according to the invention can consist of any structure having a shape that is easy to grasp, preferably in one hand so that the operator is able to use his/her other hand to actuate the injection handle. Advantageously the gripping means comprise a screw thread complementary to that present on the injection screw.

The screw thread present on the gripping means can be brought into contact with the injection screw via a driving part. Such a part can, for example, be inserted into the gripping means and provided with independent movements relative to the latter, thereby enabling the screw thread of the gripping means to be coupled to or uncoupled from the screw thread of the injection screw. It is thus possible, when the two screw threads are not coupled, to impart longitudinal translational movements to the injection screw without necessarily having to rotate it, which can save time particularly when charging the container with bone cement.

In a preferred manner, the driving part is associated with a return spring abutting against the gripping means so as to facilitate the placement in contact or separation of the screw thread present on the gripping means with the screw thread present on the injection screw. In this case, advantageously, the gripping means comprise a locking/unlocking ring associated with a pin enabling the return spring to be compressed so as to pass from the separated position to the contact position between the two screw threads.

EXAMPLE

The following examples and figures are given purely for illustrative purposes and should not be construed as any limitation of the present invention.

FIG. 1: General view, in profile and slight perspective, of the device according to the invention, with the injection screw in the inserted position, FIG. 2: General view, in profile and slight perspective, of the device according to the invention, with the injection screw in the retracted position, FIG. 3: Exploded general view, in profile and slight perspective, of the device according to the invention, FIG. 4: General sectional view on the lengthwise axis of the device according to the invention, with the injection screw in the inserted position, FIG. 5: Detail view, in profile, of the driving means in the uncoupled position, FIG. 6: Detail view, in slight perspective, of the driving means in the coupled position, FIG. 1 shows a general view of the injection device according to the invention.

The container 1 for receiving the cement to be injected has an outlet aperture at a first end 17 capable of receiving any connector 3 to deliver the cement to the target site. The second end 18 of the container 1 is capable of receiving a piston 2 (not shown in FIG. 1) set in motion by an injection screw 5 (also not shown). The container 1 is in engagement by its end 18 with gripping means 6 in the form of a handle. This general assembly is associated with the proximal portion P of the device.

The distal part D of the device, located at the other side of the gripping means 6, comprises an injection handle 13 articulated with a clamping nut 15 and a stop 16.

Figure 2:
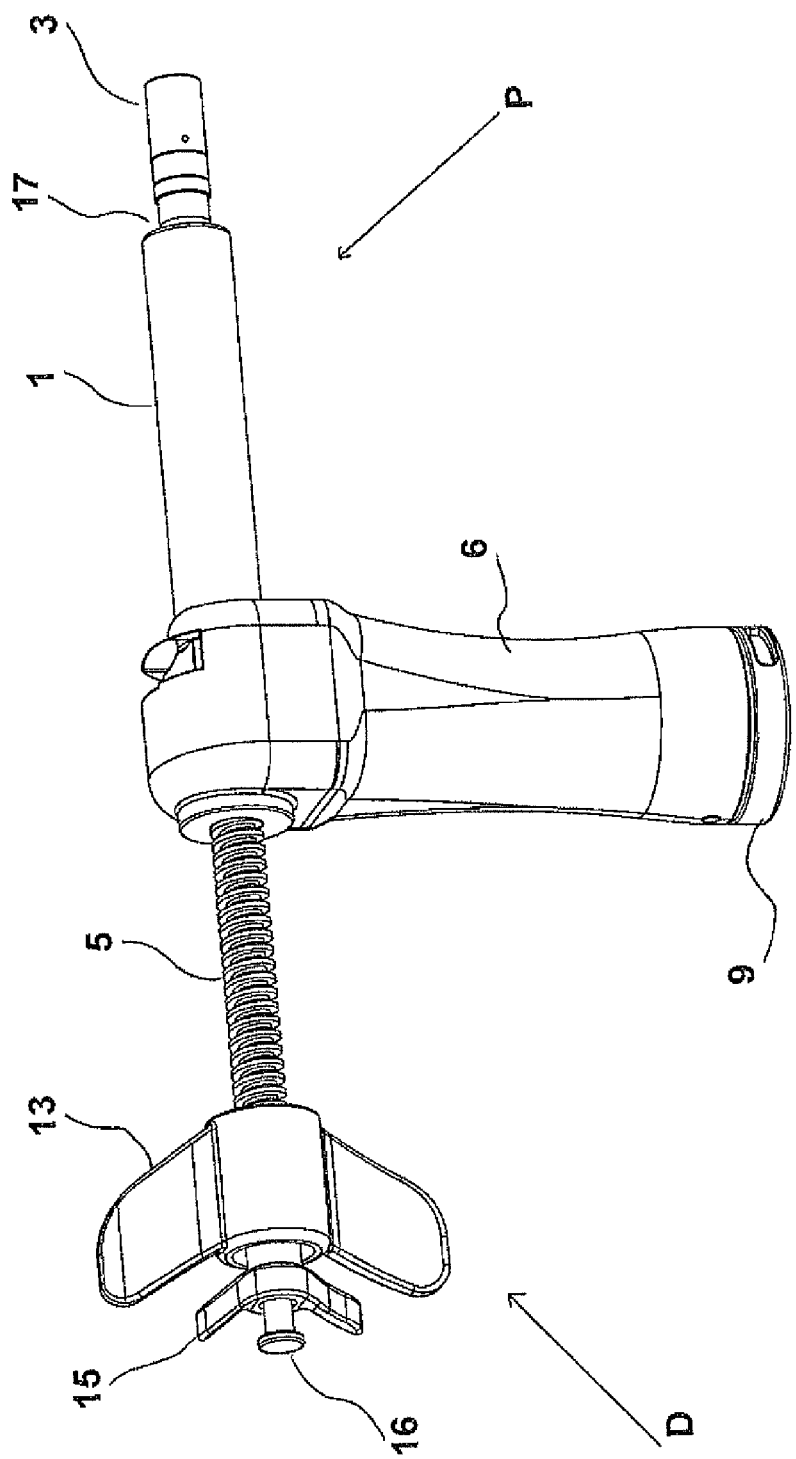

FIG. 2 illustrates the device according to the invention in the "charged" position (or ready for charging), that is with the injection screw 5 in the withdrawn position relative to the body of the container 1. The operator is thus able to introduce pre-prepared cement into the body of the container 5 by aspiration via the first end 17.

Figure 3:
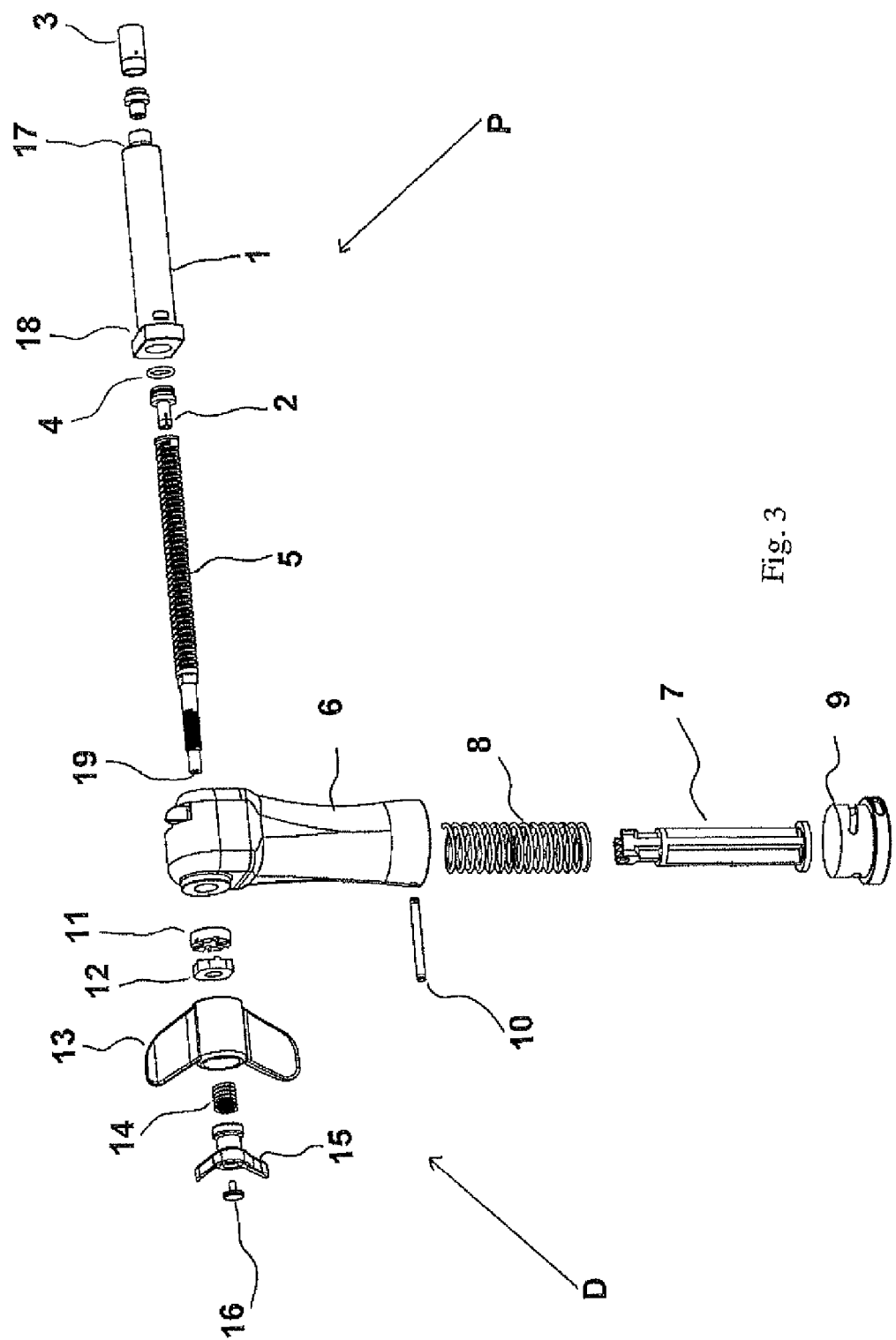

FIG. 3 serves to more precisely identify the various components of the device according to the invention by means of an exploded view. The container 1 receives the piston 2 which can be fitted with a seal 4 to facilitate efficient aspiration and ejection of cement through the end 17. The piston 2 is in integral contact with the injection screw 5. The injection screw 5 passes through the gripping means 6 via a passage such that the end 19 of the screw is located in the distal part of the device, that is to say on the other side of the gripping means 6. The distal end 19 of the injection screw receives the pair of male/female disks, the injection handle 13, the compression spring 14, the clamping means 15 and the stop 16.

The gripping means 6 have a cavity inside which a driving part 7 can be housed. The latter is in contact with a return spring 8. The gripping means 6 are closed by a locking/unlocking ring 9 for holding the driving part 7 inside the cavity and capable of receiving a pin for maintaining the locked or unlocked position.

Figure 4:
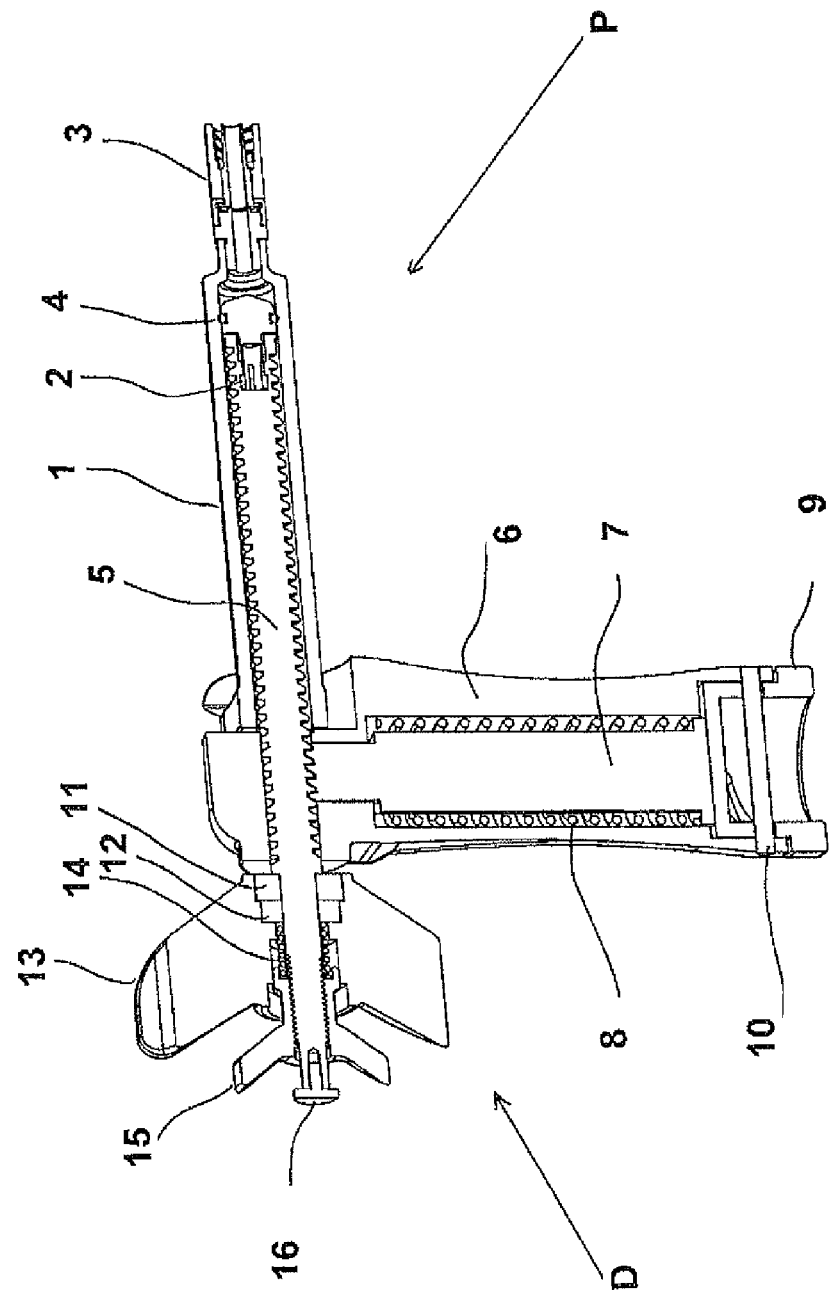

FIG. 4 serves to illustrate the arrangement of the various parts comprising the device according to the invention in relation to each other by means of a sectional view along the lengthwise axis. The device is shown in the "non-charged" position, that is with the injection screw 5 in the inserted position relative to the body of the container 1. The pair of male/female disks are coupled, the driving disk 12 is in contact with the driven disk 11 which is in turn abutted on a portion of the distal end 19 of the injection screw 5.

The gripping means 6 are in the locked position, the screw thread present on the driving part 7 is in contact with the screw thread of the injection screw 5. This position is maintained by means of the pin 10 cooperating with the ring 9.

Figure 5:
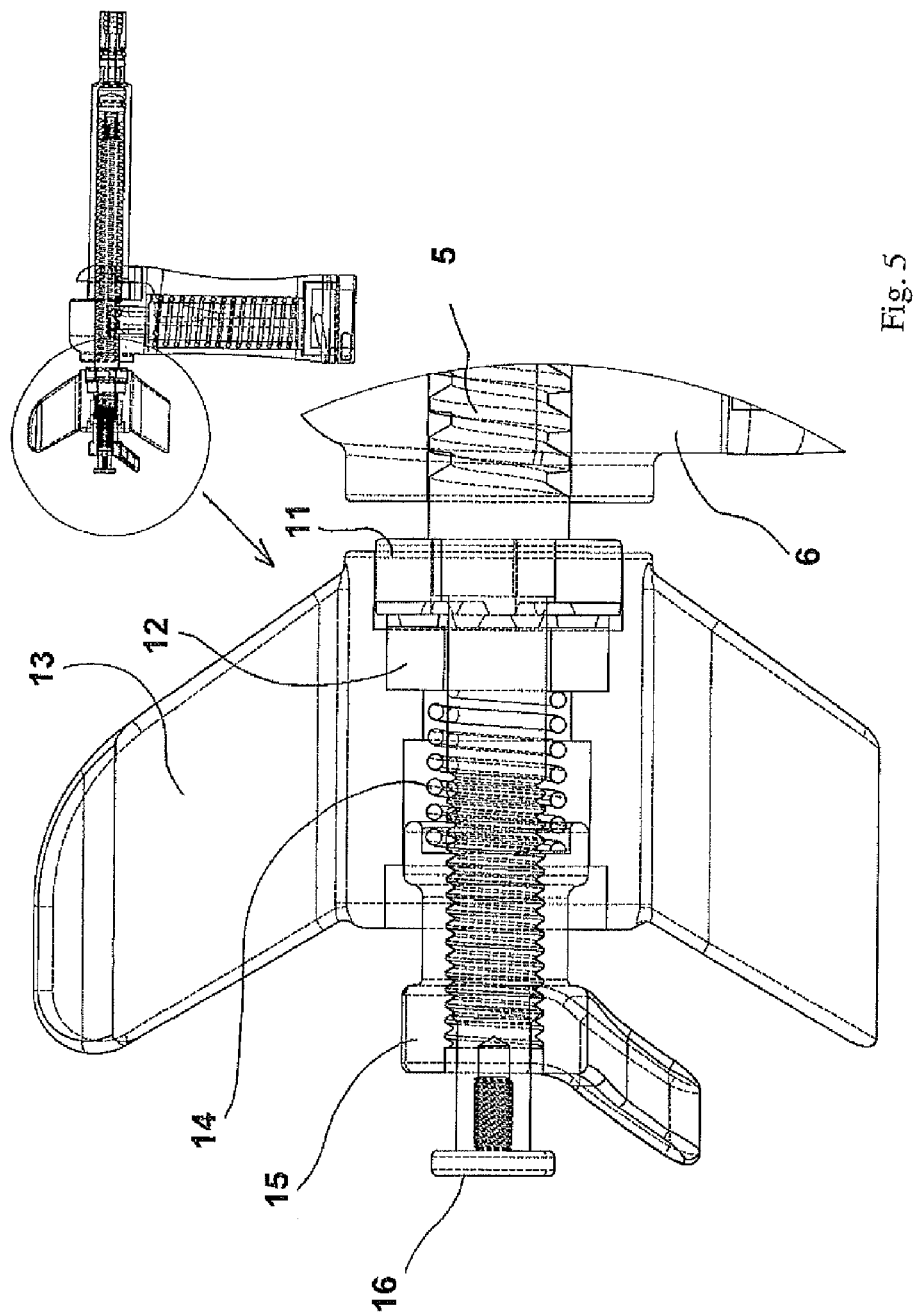

FIG. 5 illustrates in detail the driving means in the uncoupled position. The driving disk 12 is not engaged with the driven disk 11. The force exerted by the compression spring 14 on the driving disk 12 is not sufficient to set the driven disk 11 in motion.

Figure 6:
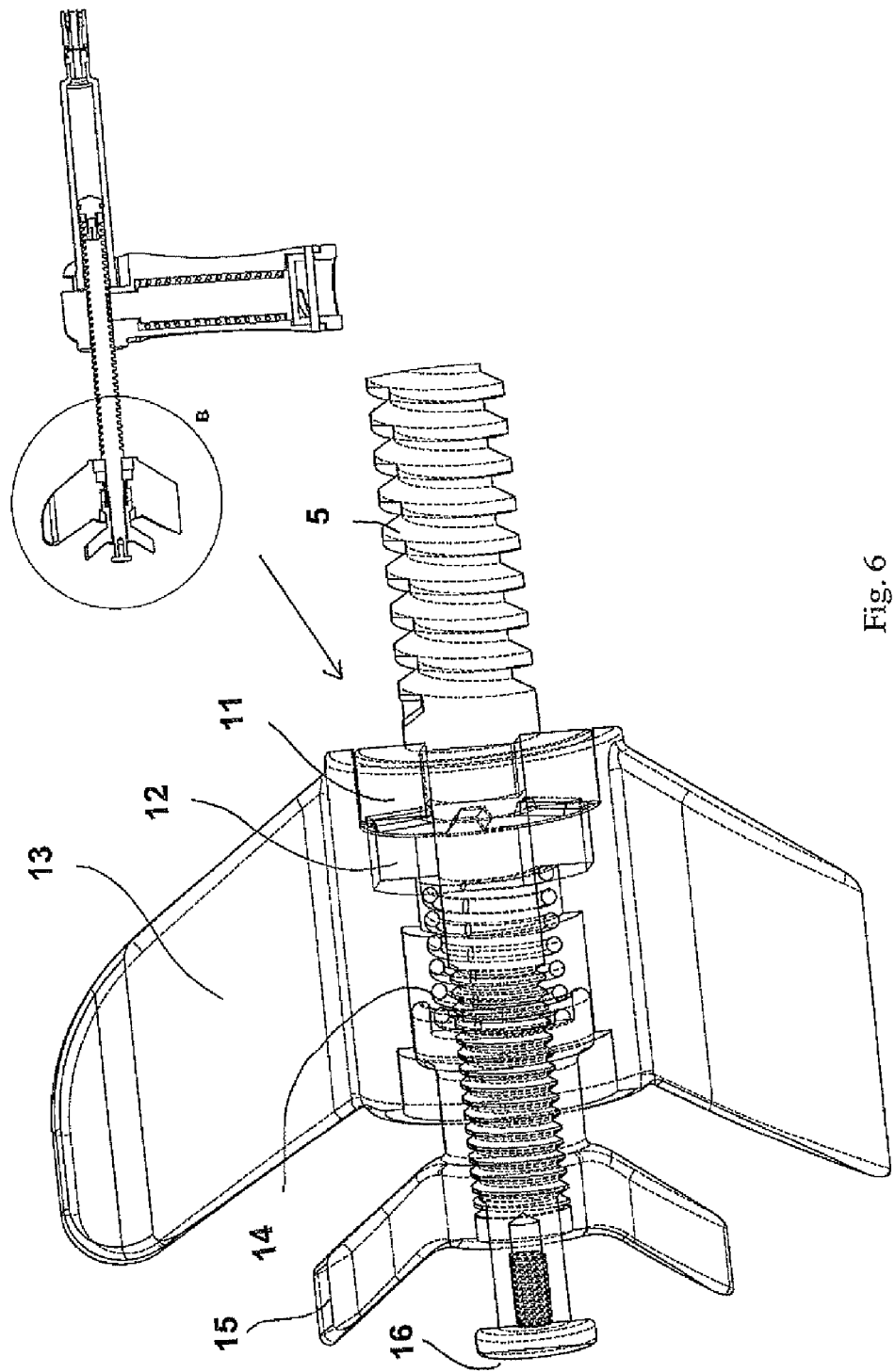

FIG. 6 illustrates in detail the driving means in the coupled position. The driving disk 12 is engaged with the driven disk 11. The force exerted by the compression spring 14 on the driving disk 12 enables the driven disk 11 to be set in motion. The latter rotatably actuates the injection screw 5 which travels in a lengthwise translational manner through the body of the container 1 by virtue of the coupling of its screw thread with the driving part 7.

Operation of the Device According to the Invention

At the start of the injection process, the pressure inside the body of the container 1 of the device is zero or virtually zero. The compression spring 14 located around the injection screw 5 is in abutment by one of its ends on the clamping nut 15 situated at the distal end 19 of the injection screw 5, the other end of the spring 14 coming into contact with the driving disk 12 integral with the rotational movements of the injection handle 13 and thus exerting pressure thereon. The initial pressure exerted at the start of the process by the compression spring 14 on the driving disk 12 causes the latter to move in a lengthwise translational manner in the passage of the handle 13 and enables it to be placed in contact with the driven disk 11.

The injection screw 5 is set in rotation by the operator by turning the injection handle 13 in the direction corresponding to the progression of the piston 2 inside the body of the container 1 defined by the screw thread provided on the gripping means 6. The movement imparted to the injection handle 13 is transmitted to the driving disk 12 which is itself in contact with the driven disk 11 under the effect of the initial pressure exerted by the spring 14. The driven disk 11 then follows the rotational movement imparted by the driving disk 12 and causes the rotation of the injection screw 5 with which it is integral.

The rotational movement of the injection screw 5 is converted into a translational movement along the longitudinal axis of the device by the interaction of the screw thread located on the injection screw 5 with the screw thread present on the gripping means 6. The injection screw 5 then progresses in a lengthwise translational manner inside the container 1 which is integral with the gripping means 6 according to the rotational movements which the operator imparts to the injection handle 13. The proximal end of the injection screw 5 is in contact with a piston 2 making it possible to pressurise the internal space of the container 1 for receiving the bone cement, also referred to as the container body.

The more the operator turns the injection handle 13, the further the injection screw 5 advances in its translational movement and the more the pressure inside the container 1 increases. Once a certain pressure threshold is reached inside the container 1, the bone cement is thus ejected from the container 1 to the outside via the outlet aperture located at the end 17. The outflow of bone cement from the container depends on the properties of the cement and in particular its level of viscosity and the pressure exerted on the inside of the body of the container 1. The more fluid the cement the more easily it is ejected from the container 1, that is under the effect of a low pressure. On the other hand, the more viscous the cement the more it is necessary to increase the pressure inside the body of the container 1 in order to eject it.

The more the pressure increases inside the body of the container 1 the greater the risk of rupture of the container wall, and the less even and controlled the outflow. To prevent such critical pressure levels being reached and to avoid the rupture of the container 1 or uncontrolled outflow, the present invention discloses a device provided with a cement injection system capable of self-locking when the pressure within the body of the container 1 exceeds a certain threshold which can be predetermined.

The greater the pressure exerted inside the body of the container 1, the greater the force required to set the injection screw 5 in rotation. From a certain pressure level defined by the mechanical strength properties of the spring 14, the force exerted by the spring 14 on the driving disk 12 is no longer sufficient to allow the latter to remain in contact with the driven disk 11 so as to cause its rotation. The driving disk 12 then follows the rotational movements transmitted by the operator to the injection handle 13, but rotates "idly" without being able to drive the driven disk 11 integral with the injection screw 5, which remains locked in position without effecting a further rotation and thus without advancing in the lengthwise direction.

When the limit pressure, defined by the spring 14, is reached inside the body of the container 1, it progressively decreases depending on the viscosity of the cement as the latter is ejected from the container 1 via the outlet aperture. The pressure thus gradually reverts to levels at which the injection screw 5 is able to advance in a lengthwise direction for much lower values of force. The driving disk 12 it then able to re-engage with the driven disk 11 so as to transmit its own rotational movement thereto, the rotational force of the driven disk 11 again becoming greater than the pressure exerted on the inside of the body of the container 1.

It is thus possible to progressively inject bone cement using the device according to the invention without reaching levels of overpressure inside the container 1 liable to cause rupture of its walls or uneven outflow. The operator can impart rotational movements to the injection handle 13 and cause the injection screw 5 to move in a lengthwise translational manner until it reaches the pressure limit level. When this level is reached, the operator can continue to turn the injection handle 13, but the latter no longer drives the driven disk 11 integral with the injection screw 5 and the injection handle 13 rotates "idly" until the pressure level within the body of the container 1 reverts to values enabling the driven disk 11 to be driven by the driving disk 12.

Advantageously, it is possible to adjust the limit pressure above which the driven disk 11 will no longer be set in motion by the driving disk 12 by adjusting the level of force that the compression spring 14 imparts to the driving disk 12. This can be achieved by selecting the quality of the compression spring 14 and the level of force that it is able to transmit, depending on its nature and its length for example. In a particular embodiment of the invention, the injection device includes means making it possible to reduce the length of the compression spring. A clamping nut 15 bearing on the injection screw 5 can thus be provided to easily reduce the length of the compression spring 14.

Depending on the viscosity of the cement to be injected and the level of overpressure that the container 1 can withstand, it is possible to easily modify the distance over which the spring 14 can compress and expand. The more this length is reduced the more easily the driving disk 12 is able to rotate the driven disk 11, at elevated levels of pressure within the body of the container 1. The greater the length over which the spring 14 is able to expand the less driving disk 12 will be able to set the driven disk 11 in rotation.

The invention claimed is:

1. Device for the injection of bone cement comprising a reservoir container for receiving the said bone cement, having a first end comprising an outlet aperture for the injection of cement and a second end receiving a piston capable of performing longitudinal translational movements inside the body of the container, the said piston being set in motion via an injection screw projecting from the body of the reservoir and engaging with gripping means designed to be placed integrally in contact with the container, characterised in that it comprises means for rotatably driving the injection screw capable of self-locking depending on the pressure inside the container body, the said means for rotatably driving the injection screw comprising a handle having a passage receiving the injection screw and articulated therewith via a pair of male/female disks, one of the two disks, referred to as the driving disk, being integral with the rotational movements of the handle and designed to perform translational movements on the longitudinal axis of the passage in the handle, the other disk, referred to as the driven disk, being integral with the rotational movements of the injection screw, the driving disk coming into contact with the driven disk under the effect of a compressive force exerted on the distal part of the injection screw.

2. Device for the injection of bone cement according to claim 1, characterised in that the two disks come into contact with one another by means of a compression spring having one end in abutment at the distal part of the injection screw, the other end of the spring coming into contact, directly or indirectly, with the driving disk.

3. Device for the injection of bone cement according to claim 2, characterised in that the distal part of the injection screw has clamping means enabling the compression distance of the spring to be adjusted.

4. Device for the injection of bone cement according to claim 3, characterised in that the gripping means comprise a screw thread complementary to that present on the injection screw.

5. Device for the injection of bone cement according to claim 2, characterised in that the gripping means comprise a screw thread complementary to that present on the injection screw.

6. Device for the injection of bone cement according to claim 1, characterised in that the gripping means comprise a screw thread complementary to that present on the injection screw.

7. Device for the injection of bone cement according to claim 6, characterised in that the screw thread present on the gripping means is brought into contact with the injection screw via a driving part.

8. Device for the injection of bone cement according to claim 7, characterised in that the driving part is associated with a return spring abutting against the gripping means.

9. Device for the injection of bone cement according to claim 8, characterised in that the gripping means comprise a locking/unlocking ring associated with a pin enabling the return spring to be compressed.

\* \* \* \* \*